(12) United States Patent
Carrico (10) Patent No.: US 11,684,782 B2
(45) Date of Patent: *Jun. 27, 2023

(54) SYSTEMS AND METHODS FOR ELECTRO-THERAPY TREATMENT

(71) Applicant: TKBMN, LLC, Lawrenceburg, IN (US)

(72) Inventor: Thomas J. Carrico, Westfield, IN (US)

(73) Assignee: TKBMN, LLC, Lawrenceburg, IN (US)

( * ) Notice: Subject to any disclaimer, the term of this patent is extended or adjusted under 35 U.S.C. 154(b) by 266 days.

This patent is subject to a terminal disclaimer.

(21) Appl. No.: 17/014,450

(22) Filed: Sep. 8, 2020

(65) Prior Publication Data

US 2020/0398059 A1    Dec. 24, 2020

Related U.S. Application Data

(63) Continuation of application No. 15/981,082, filed on May 16, 2018, now Pat. No. 10,792,500.

(51) Int. Cl.
| | |
|---|---|
| *A61N 1/36* | (2006.01) |
| *A61B 5/00* | (2006.01) |
| *A61N 1/04* | (2006.01) |
| *A61B 5/352* | (2021.01) |

(52) U.S. Cl.
CPC ........ *A61N 1/36171* (2013.01); *A61B 5/4035* (2013.01); *A61B 5/4836* (2013.01); *A61N 1/36031* (2017.08); *A61N 1/36034* (2017.08); *A61N 1/36114* (2013.01); *A61N 1/36139* (2013.01); *A61B 5/352* (2021.01); *A61N 1/0456* (2013.01); *A61N 1/36053* (2013.01)

(58) Field of Classification Search
CPC ............ A61N 1/36171; A61N 1/36031; A61N 1/36034
USPC .......................................................... 607/59
See application file for complete search history.

(56) References Cited

U.S. PATENT DOCUMENTS

| | | | |
|---|---|---|---|
| 6,017,302 A | 1/2000 | Loos | |
| 8,066,637 B2 | 11/2011 | Childre et al. | |
| 9,610,443 B1 | 4/2017 | Dean et al. | |
| 2013/0245486 A1* | 9/2013 | Simon | A61B 5/4836 607/46 |

* cited by examiner

*Primary Examiner* — Lynsey C Eiseman
*Assistant Examiner* — Jessica L Mullins
(74) *Attorney, Agent, or Firm* — Brannon Sowers & Cracraft PC (57) ABSTRACT

A system for electro-therapeutically treating a patient includes a stimulatory device electromagnetically coupled with the nervous system of a patient, an electrical power supply, and a control mechanism structured to energize the stimulatory device by way of the electrical power supply at a stimulation frequency. The control mechanism is further structured to control the energizing so as to produce a treatment signal encoded in the energizing and having a treatment signal frequency equal to or less than the stimulation frequency.

14 Claims, 4 Drawing Sheets

SYSTEMS AND METHODS FOR ELECTRO-THERAPY TREATMENT

TECHNICAL FIELD

The present disclosure relates generally to electro-therapy, and more particularly to electro-therapy entraining the autonomic nervous system of a patient to an encoded treatment signal.

BACKGROUND

There have been significant technical and scientific advancements in the fields of cardiovascular research, neurology, neuroscience, electrophysiology, and others in recent years. While much of the research is in its infancy, recent developments relating to a greater understanding of the role and importance of systemic resonance frequencies in the human body, and their effect on and relationship with heart rate variability (HRV), have shown promise in supporting the development of improved and altogether new strategies for treating disease and improving the health of human beings.

HRV is believed to represent one physiological parameter by which frequency phenomena in the human body are observable. Power spectral analysis is used to separate the complex HRV waveform into its component rhythms. Spectral analysis provides information about how power is distributed as a function of frequency. Those skilled in the art will be familiar with the division of the power spectrum into a plurality of frequency bands. Electrical activity of the nervous system in these bands is understood to have certain relationships with patient health, in particular the autonomic nervous system. The autonomic nervous system is generally divided into the parasympathetic and sympathetic nervous systems. The relative level of stimulation by way of each of these systems as well as their balance and tone understood to be indicative of various human health conditions. There have been proposals in recent years to utilize biofeedback in an attempt to train patients to modulate their autonomic nervous system function. Such techniques appear to have merit; however, advancements would be readily accepted in the field.

SUMMARY OF THE INVENTION

In one aspect, a method of electro-therapeutically treating a patient includes energizing a stimulatory device electromagnetically coupled with the nervous system of the patient, at a stimulation frequency. The method further includes controlling the energizing of the stimulatory device so as to encode a treatment signal in the energizing of the stimulatory device, the treatment signal having a treatment signal frequency that is equal to or less than the stimulation frequency. The method further includes entraining the autonomic nervous system of the patient to the treatment signal, so as to adjust a power spectral density of the autonomic nervous system toward a target power spectral density.

In another aspect, a method of electro-therapeutically treating a patient includes receiving data indicative of electrical activity of the autonomic nervous system of the patient, comparing the data with a stored model, and outputting a diagnostic signal based on the comparing of the data with a stored model. The method further includes energizing at least one stimulatory device structured to electromagnetically couple with the nervous system of the patient, at a stimulation frequency, responsive to the diagnostic signal. The method further includes controlling the energizing of the at least one stimulatory device so as to encode a treatment signal at a treatment signal frequency that is equal to or less than the stimulation frequency.

In still another aspect, a system for electro-therapeutically treating a patient includes at least one stimulatory device structured to electromagnetically couple with the nervous system of the patient, and an electrical power supply coupled with the at least one stimulatory device. The system further includes a control mechanism structured to energize the at least one stimulatory device by way of the electrical power supply at a stimulation frequency. The control mechanism is further structured to control the energizing of the at least one stimulatory device so as to produce a treatment signal encoded in the energizing of the at least one stimulatory device and having a treatment signal frequency that is equal to or less than the stimulation frequency.

In still another aspect, a device for electro-therapeutically treating a patient includes a stimulatory device structured to electromagnetically couple with the nervous system of the patient, and a control mechanism for the stimulatory device including a computer, and a computer readable memory containing computer executable program instructions, and the control mechanism is structured by way of execution of the computer executable program instructions to: control an electrical power supply coupled with the stimulatory device, such that the stimulatory device is energized at a stimulation frequency that is about 1 Hz or greater, and control the energizing of the stimulatory device so as to encode a treatment signal at a treatment signal frequency that from about 0.001 Hz to about 1 Hz.

DETAILED DESCRIPTION

Figure 1:
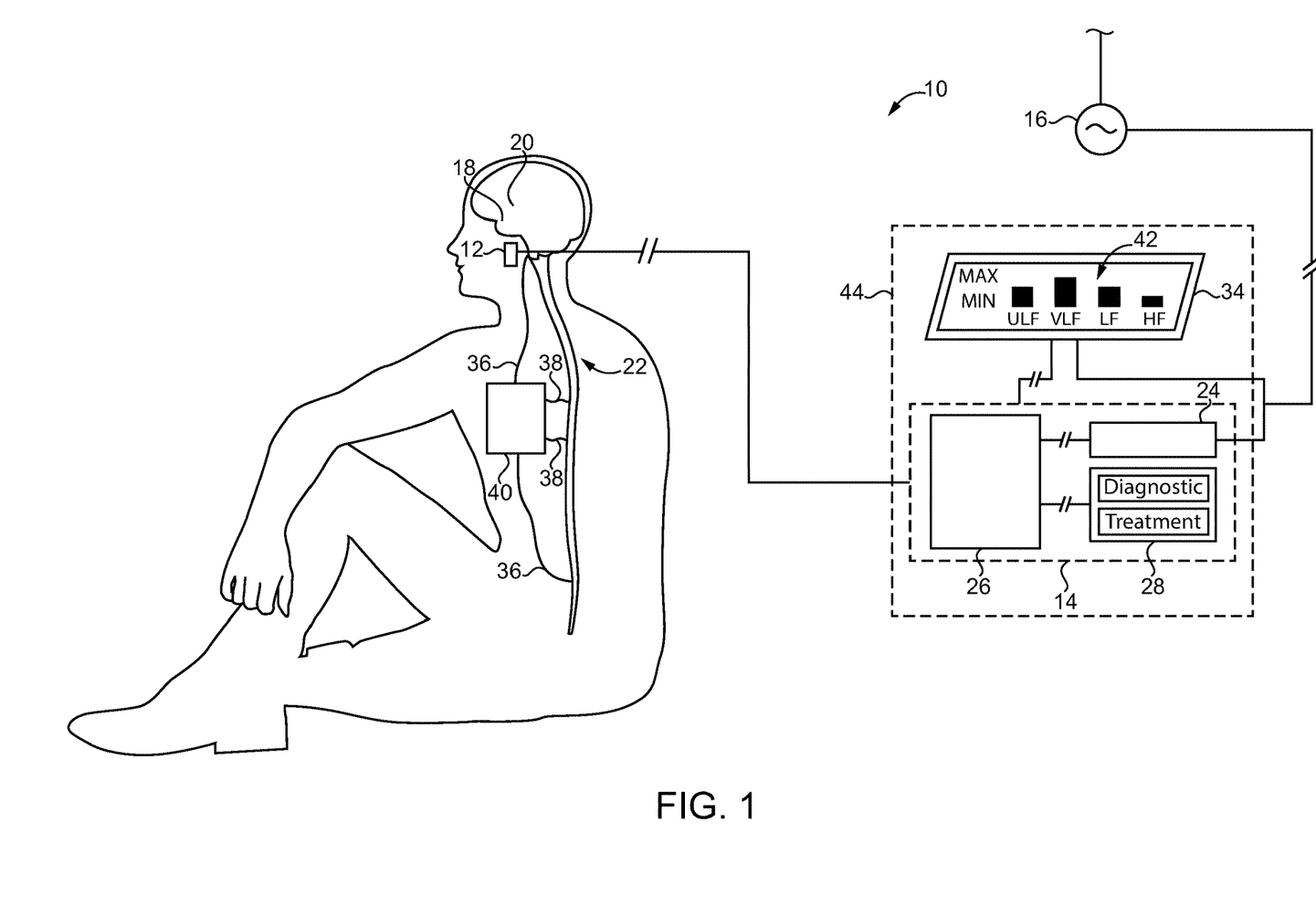
FIG. 1 is a system level diagram of a system for electro-therapeutically treating a patient, according to one embodiment.

Referring to FIG. 1, there is shown a system 10 for electro-therapeutically treating a patient. System 10 may include at least one stimulatory device 12 structured to electromagnetically couple with the nervous system 22 of the patient. In an implementation, the at least one stimulatory device (hereinafter "device") 12 includes an electrode (not shown) in contact with the body of the patient and implanted or in contact with the patient's skin, for example. Device 12 could include a vagal stimulator, a spinal cord stimulator, an auricular stimulator, a deep-brain stimulator, a non-contact transcranial stimulator, or any other device suitable for stimulating a patient's nervous system. The illustration in FIG. 1 depicts device 12 as it might appear where implemented as a trans-cutaneous stimulator positioned to stimulate the auricular branch of the vagus nerve, and is shown as a single device. It should be appreciated that the description herein of device 12 in the singular is intended to also encompass implementations where plural devices are used. Moreover, positioning of device 12 as depicted in FIG. 1 should be understood to disclose by analogy other configurations or positioning of the one or more stimulatory devices. Those skilled in the art will readily conceptualize how device 12 might be configured and placed in a vagal stimulatory application or a spinal cord stimulator application, for instance. It will further be appreciated that certain implementations of system 10 might employ nervous system stimulation strategies that may not require device 12, such as, for instance, stimulation strategies that use magnetic or sound frequency delivery systems.

In FIG. 1, the autonomic nervous system (ANS) 22 is depicted as including both parasympathetic connections 36 and sympathetic connections 38 to one or more organs or locations 40, such as the lungs, heart, stomach, intestines, kidneys, pancreas, the adrenal or parotid glands, or any other organ, tissue, system, or location innervated by the ANS. It should be appreciated that the illustration of the nervous system 22 in FIG. 1 is illustrative only, and from the following description it will be apparent that other systems and subsystems of the human body can affect and be affected by electro-therapy treatment in the manner contemplated herein. In FIG. 1 the patient's amygdala and hypothalamus and amygdala are shown with reference numerals 18 and 20, respectively. Without being bound by theory, electrical stimulation according to the prescribed manner disclosed herein is understood to stimulate the central nervous system (CNS) of the patient in a manner that triggers a cascade of events originating at the amygdala 18 and hypothalamus 20 that induces beneficial and at least temporarily lasting changes in the electrical activity of the ANS, bringing about improvement or alleviation of a variety of different medical or psychological conditions of the patient.

To this end, system 10 further includes a control mechanism 14 that is coupled with an electrical power supply 16 and with device 12, and structured to energize device 12 by way of electrical power supply 16 at a stimulation frequency. In an implementation, control mechanism 14 includes power circuitry 24 electrically coupled between device 12 and electrical power supply 16, and includes switches (not shown) that can be controlled in a manner to produce the desired stimulation frequency. The stimulation frequency might be from about 1 Hz to about 14 Hz, consistent with frequencies known as delta, theta, and alpha frequencies in the human body. The present disclosure is not limited with regard to the stimulation frequency, however, and frequencies above this range or below this range could be applied within the present context. For example, embodiments are contemplated where the stimulation frequency is from about 15 Hz to about 10,000 Hz.

Control mechanism 14 further includes a computer processor 26, including any suitable data processing device such as a microprocessor or a field programmable gate array (FPGA). Processor 26 may be in control communication with power circuitry 24 and structured to control the energizing of device 12 so as to produce a treatment signal encoded in the energizing of device 12 and having a treatment signal frequency that is different from, and typically less than, the stimulation frequency. Another way to understand the operating principles of control mechanism 14 is that device 12 can be controlled such that the turning-on and turning-off (or other modulation such as varying of amplitude) of electrical power to device 12 encodes a treatment signal whereby the nervous system 22 of the patient is stimulated in a manner believed to bring about the desired positive results noted above and further discussed below.

Control mechanism 14 may further include a computer readable memory 28 that stores computer executable program instructions that, upon execution by processor 26, cause electrical power supply 16 or power circuitry 24 to behave in a manner that may result in energizing device 12 at the stimulation frequency. Memory 28 could include RAM, ROM, DRAM, SDRAM, Flash, or still another type of memory. Execution of the computer executable program instructions can further cause processor 26 to control the energizing of device 12 so as to encode the treatment signal at a treatment signal frequency equal to or less than the stimulation frequency. As noted above, the treatment signal may include electrical pulses produced by device 12 in a time-varying pattern that defines the treatment signal frequency.

Treatment protocols may be used by processor 26 to control power circuitry 24 and/or electrical power supply 16 in a particular way, examples of which are set forth below. In a practical implementation strategy, system 10 may be structured for electro-therapeutically treating a patient according to a plurality of different available treatment protocols that may be stored in memory 28 and executed to treat a patient having any conditions, symptoms, or states caused by or associated with a type of autonomic dysfunction categorized within a predefined zone. It has been observed that conditions, symptoms, or states implicating the ANS may be associated or otherwise correspond with imbalances in parasympathetic nervous system (PNS) activity or in sympathetic nervous system (SNS) activity. For instance, each of SNS activity and PNS activity might be higher or lower than a normal or expected level of activity. In an implementation, such imbalances can be categorized in to 8 discrete zones, each zone representing a characteristic type of autonomic dysfunction. A first zone ("Zone 1") may be characterized by high PNS activity and low SNS activity, a second zone ("Zone 2") by high PNS activity and normal SNS activity, a third zone ("Zone 3") by high dual autonomic tone, a fourth zone ("Zone 4") by high SNS activity and normal PNS activity, a fifth zone ("Zone 5") by high SNS activity and low PNS activity, a sixth zone ("Zone 6") by normal SNS activity and low PNS activity, a seventh zone ("Zone 7") by low SNS activity and low PNS activity, and an eighth zone ("Zone 8") by low SNS activity and normal PNS activity. Those skilled in the art will appreciate that a great many of medical or psychological conditions, symptoms, or states implicating the ANS are often associated with autonomic dysfunction characterized by one of these 8 zones. Accordingly, system 10 might be able to provide diagnostic information responsive to observed imbalances in PNS activity and SNS activity. Put differently, system 10 might be structured to gather diagnostic information by monitoring or otherwise receiving data indicative electrical activity in a patient and cause control mechanism 14 to output a diagnostic signal.

It will further be appreciated that by comparing the electrical activity observed with stored patterns, control mechanism 14 can be structured to make a determination as to a treatment protocol to be applied in treating the patient, and can execute that treatment protocol in a manner that is responsive to the diagnostic signal. In this way, control mechanism 14 might select a treatment protocol by matching the condition, symptom, or state to be treated with the corresponding zone. By way of example, if, for instance, a certain condition, symptom, or state typically corresponds with high SNS activity and normal PNS activity, a patient suffering from that condition may be treated by selecting the treatment protocol associated with Zone 4. Those skilled in the art will understand that at least some of the conditions implicating the ANS can be understood as a dysautonomic state or dysautonomia in the patient. Other zones than those specifically described might be observed, including zones not listed, or not yet discovered or recognized. Some embodiments may include zones within each of the listed zones (e.g., subzones) based upon particular electrical activity profiles that are observed.

Those skilled in the art will nevertheless appreciate that in many instances the state of the patient's health, and which of a plurality of different zones the patient falls into, can be determined without any need to sense or directly monitor electrical activity in the ANS of the patient. For example, a variety of conditions are known which are well recognized as having associations with the ANS imbalances observed in Zones 1-8, which may allow a clinician to select a treatment protocol based on observed or described symptoms or conditions. As such, in an embodiment, a medical professional or clinician might select a treatment protocol based on a diagnosed, observed, or suspected condition, symptom, or state. In other words, system 10 could be structured to allow a medical professional or clinician to select a treatment protocol without consulting data indicative of a patient's ANS. In such an embodiment, control mechanism 14 might not output the diagnostic signal.

Conversely, system 10 could also be structured to function in a purely diagnostic manner. In such an embodiment, control device 14 might output the diagnostic signal based at least in part upon similarity between the data indicative of electrical activity in the patient and the stored model, or differences between the data that is received and the stored model. The diagnostic signal could be structured to cause diagnostic information to be displayed on a display 34. For instance, system 10 could output a display message that a patient's ANS activity is indicative of autonomic dysfunction characterized by one of the 8 Zones mentioned above, which may assist the medical professional or clinician in diagnosing the patient.

In the exemplary embodiment illustrated in FIG. 1, control mechanism 14 is structured to generate both the diagnostic signal and the treatment signal. System 10 may be structured to receive data indicative of electrical activity of a patient's ANS and, based on the data, determine which of a plurality of different possible states of autonomic dysfunction, or states of normal functioning, are present in or experienced by the patient. For instance, in an implementation, device 12 can include a sensory device or electrical probe, electromagnetically coupled with the patient's nervous system 22 and structured to monitor electrical activity of the patient's ANS. Control mechanism 14 may be structured to receive the data, and compare the data with a stored model of at least one pattern of electrical activity, which may include a plurality of zones each characteristic of a type of autonomic dysfunction, and generate the diagnostic signal responsive thereto. For example, control mechanism 14 might be structured to detect an ANS imbalance and categorize the detected imbalance as within one of a number of the 8 Zones discussed above and generate a diagnostic signal indicative of the proper Zone.

Figure 2:
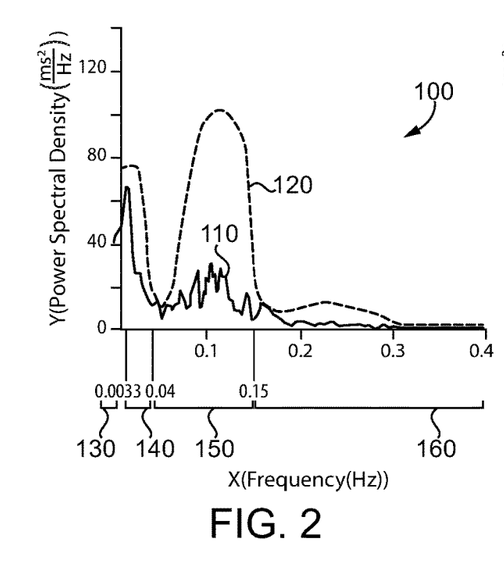
FIG. 2 is a graph of power spectral density of autonomic nervous system activity in comparison with a target power spectral density.

Referring now to FIG. 2, there is shown a graph 100 illustrating example power spectral density (ms$^2$/Hz) on the Y-axis in comparison to frequency (Hz) on the X-axis. A first signal 110 represents electrical activity that might be observed in a patient prior to treatment. A second signal or target signal is shown at 120 and represents what might be expected to be observed at least in a normalized sense in a healthy individual. It should be appreciated that graph 100 and others herein are purely illustrative. Electrical activity in the human nervous system can be highly dynamic, and thus the signal patterns that might be observed prior to treatment could vary significantly from what is depicted in FIG. 2. Moreover, some patterns known to be indicative of certain disease states, or other states in a patient's nervous system, might not be evident all the time, and analysis over a period of minutes, hours, or even longer might be necessary for a signal pattern indicative of an imbalance, overstimulation or under-stimulation at certain frequencies, or other signal properties of interest to be observed. Analogously, detection of signal patterns that might be observed after treatment, and indicative of changes in electrical activity patterns that occur in response to treatment, may not be apparent in an instantaneous recording and instead require observation for a period of time or under certain conditions. For these reasons it will be appreciated that the signal patterns shown in FIG. 2, and others discussed herein, might or might not be observed or might differ significantly from those observed, in an actual clinical setting.

Signal 120 may be understood as a target spectral density. The frequency range on the X-axis is divided into a plurality of bands, including an ultra-low frequency or ULF band 130 that is about 0.0033 Hz or less, a very low frequency or VLF band 140 from about 0.0033 Hz to about 0.04 Hz, a low frequency or LF band 140 from about 0.04 Hz to about 0.15 Hz, and a high frequency or HF band 160 is from about 0.15 Hz to about 0.4 Hz. It can be seen from FIG. 2 that a relatively large difference in electrical activity in the low frequency band is observed between the target signal 120 and the observed signal 110 within LF band 150, whereas a more modest difference, while still significant, is observed in the HF band 160, and a still smaller difference is observed in ULF and VLF bands 130, 140. Control mechanism 14, or potentially a clinician, could observe that the differences between signal 110 and signal 120 are indicative of a particular condition. For instance, it has been observed that patients experiencing post-traumatic stress disorder or PTSD are characterized by under stimulation in the LF band 150 and over stimulation in the ULF 130 band or below. Hypertension can be characterized by too much sympathetic stimulation and thus a spike in the ULF band 130. Sleep disorders are known to be characterized by too much sympathetic stimulation or not enough parasympathetic stimulation associated with excessive sleepiness or problems sleeping, respectively. Anger and aggression disorders or states may be associated with sympathetic overstimulation. Future discoveries are expected to identify and elucidate a great many different ANS states that are associated with disease, psychological problems, immune system function, environmental sensitivity, pain, and human physical and mental performance. The present disclosure contemplates electro-therapy treatment of hundreds and potentially thousands of human and potentially non-human animal ANS conditions.

Figure 3:
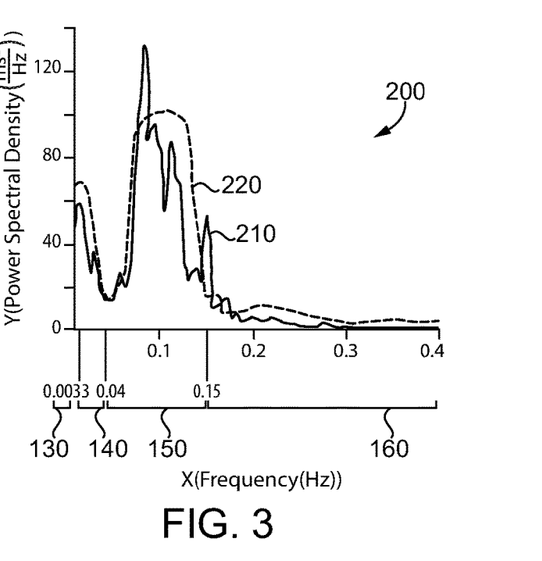
FIG. 3 is a graph of power spectral density of electrical activity in the autonomic nervous system having been adjusted by way of entrainment according to the present disclosure, in comparison with the target power spectral density.

Referring to FIG. 3, there is shown a graph 200 illustrating signal 120 in comparison with a signal 210 that might be observed in a patient after treatment according to the present disclosure. Graph 200 includes ULF, VLF, LF, and HF bands, 130, 140, 150, and 160, respectively, with each extending the same range of frequencies identified above with reference to graph 100. It can be seen that activity is increased in signal 210 in HF band 160 and in LF band 150, and less difference in magnitude is evident between the two signals generally. Graph 200 represents conditions that might be observed where the patient has been treated according to the present disclosure and ANS imbalance or dysfunction has been reduced. It will be recalled that a plurality of different treatment protocols may be stored on memory 28, and that control mechanism 14 can control device 12 to stimulate the nervous system of the patient in a manner that is based on the treatment protocol selected. In the example set forth in FIGS. 2 and 3 the patient might be stimulated, among other things, with treatment signal frequencies within LF band 150. Through entrainment of the nervous system and resonant systems of the body generally to the treatment signal in the appropriate frequency range, ANS function can be shifted in a manner such that imbalance between the PNS and SNS is reduced, under stimulation in the PNS or SNS is reduced, high dual autonomic tone is attenuated, or any other undesired pattern of electrical activity in the ANS molded towards a target level or pattern of electrical activity. In an implementation, entraining a patient's ANS to the treatment signal can be understood to adjust a power spectral density of the ANS toward a target power spectral density. In the example of FIGS. 2 and 3 the actual or observed power spectral density is represented prior to treatment by signal 110, and after treatment by way of signal 210. The target power spectral density is shown in each case by way of signal 120.

As suggested above, different conditions identified by Zones 1-8, or other zones not specifically disclosed herein, can be treated in different ways. For instance, conditions identified by Zone 1 could be treated by treatment signals provided to device 12 within frequency ranges of ULF and VLF bands 130 and 140, respectively, to target an increase in sympathetic activity, coupled with treatment signals with the frequency range of LF band 150 to target an increase in activity at homeostatic frequencies. Conditions identified by Zone 2 could include treatment with treatment signal frequencies within LF band 150. To treat conditions identified by Zone 3 treatment signal frequencies within LF band 150 might be used, potentially for the purpose of performance enhancement. To treat conditions identified by Zone 4 treatment signal frequencies within LF band 150 to target homeostasis could be applied. To treat conditions identified by Zone 5 treatment signal frequencies within HF band 160 to target an increase in parasympathetic activity could be applied, and also with treatment signal frequencies within LF band 150 to target homeostasis. To treat conditions identified by Zone 6 treatment signal frequencies within HF band 160 to target an increase in parasympathetic activity, with treatment signal frequencies within LF band 150 could be applied. To treat conditions identified by Zone 7 treatment signal frequencies within ULF and VLF bands 130 and 140, respectively, coupled with treatment signal frequencies within HF band 160 to target increase in parasympathetic activity, potentially also with treatment signal frequencies within LF band 150 to target homeostasis could be applied. To treat conditions identified by Zone 8, treatment signal frequencies within LF band 150 coupled with treatment signal frequencies within ULF band 130 and VLF band 140 could be applied to target an increase in sympathetic activity.

It will be appreciated from the foregoing discussion that the stimulation frequency (i.e., the electromagnetic frequency by which energizing of device 12 actually occurs) is not understood as the frequency employed to treat the patient, at least not with respect to ANS entrainment to adjust power spectral density. The frequencies understood to effect entrainment and coherence of ANS activity are lower frequencies, and in some instances may be frequencies lower than standard electro-therapy treatment equipment can readily generate. Some equipment could be structured to generate treatment signal frequencies that are equal to or less than a corresponding stimulation frequency. The encoding of the treatment signal in the controlled energizing of device 12 provides a mechanism for stimulating the nervous system and ultimately bringing about electrical activity of a desired spectral density in a manner that would otherwise not be possible or at least not practicable with conventional equipment. As discussed above, applying electrical stimulation to the nervous system of a patient is understood to trigger a cascade of events originating in the patient's CNS that ultimately causes the desired electrical activity in desired spectra to come about by way of entrainment.

Frequencies understood as the signature frequencies of parasympathetic activity and sympathetic activity can be observed, for example, in the heart rate variability (HRV) patterns of the patient. It has been observed that the PNS produces a rhythm at least under certain conditions according to a cycle of about 4.5 seconds or about 0.225 Hz. Encoding a treatment signal as discussed herein in this frequency range can entrain the electrical activity of the nervous system in a manner that modulates parasympathetic activity. In other words, by encoding a treatment signal at the frequencies observed in the rhythm of the PNS, an increase in electrical activity of the PNS due to the entraining effect can be expected to be observed.

Figure 4:
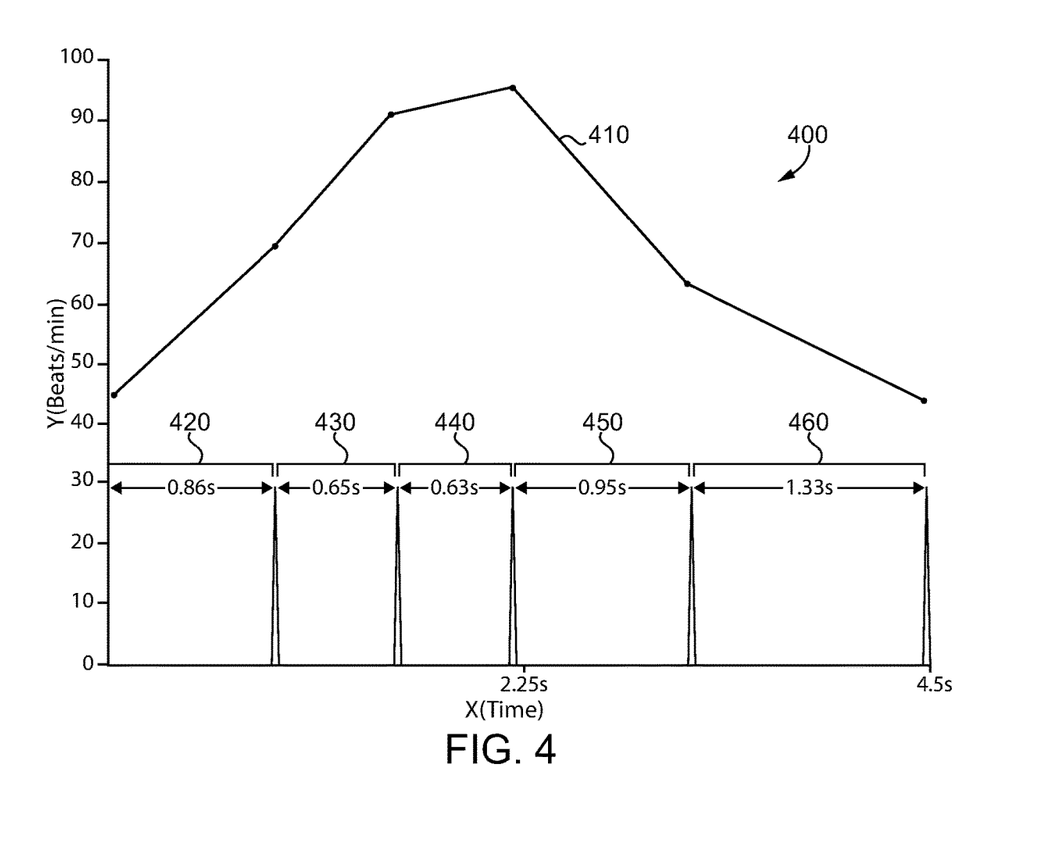
FIG. 4 is a graph of a time-varying pattern of electrical signals and heart rate variability over time where autonomic nervous system function is entrained according to a first treatment signal.
Figure 5:
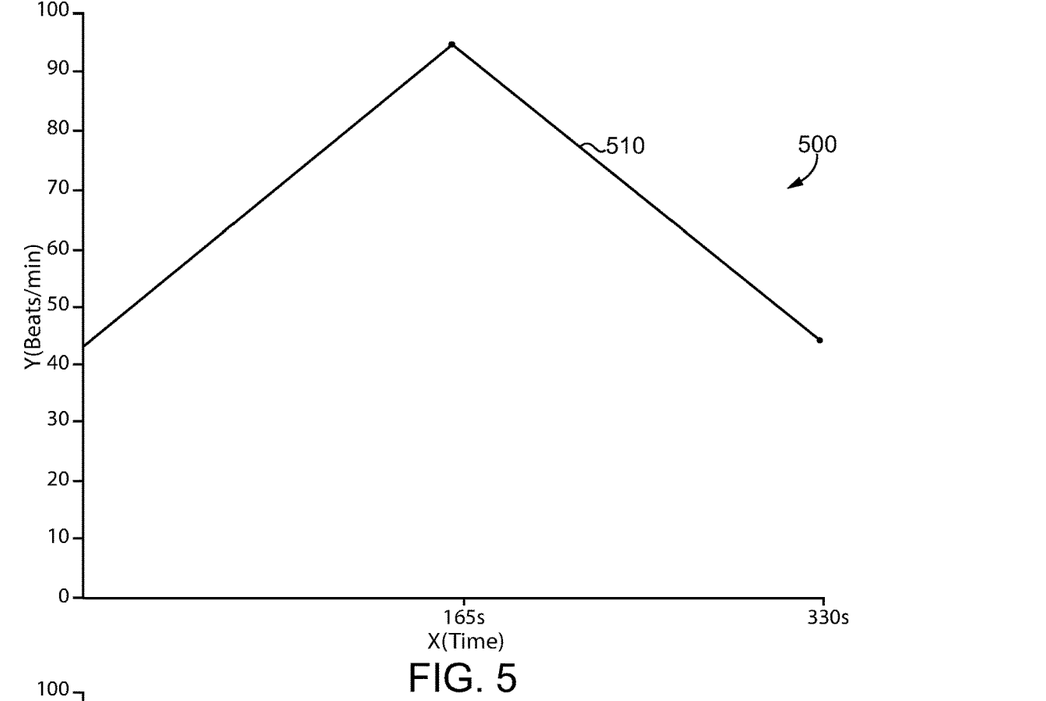
FIG. 5 is a graph of a time-varying pattern of electrical signals and heart rate variability over time where autonomic nervous system function is entrained according to a different treatment signal.
Figure 6:
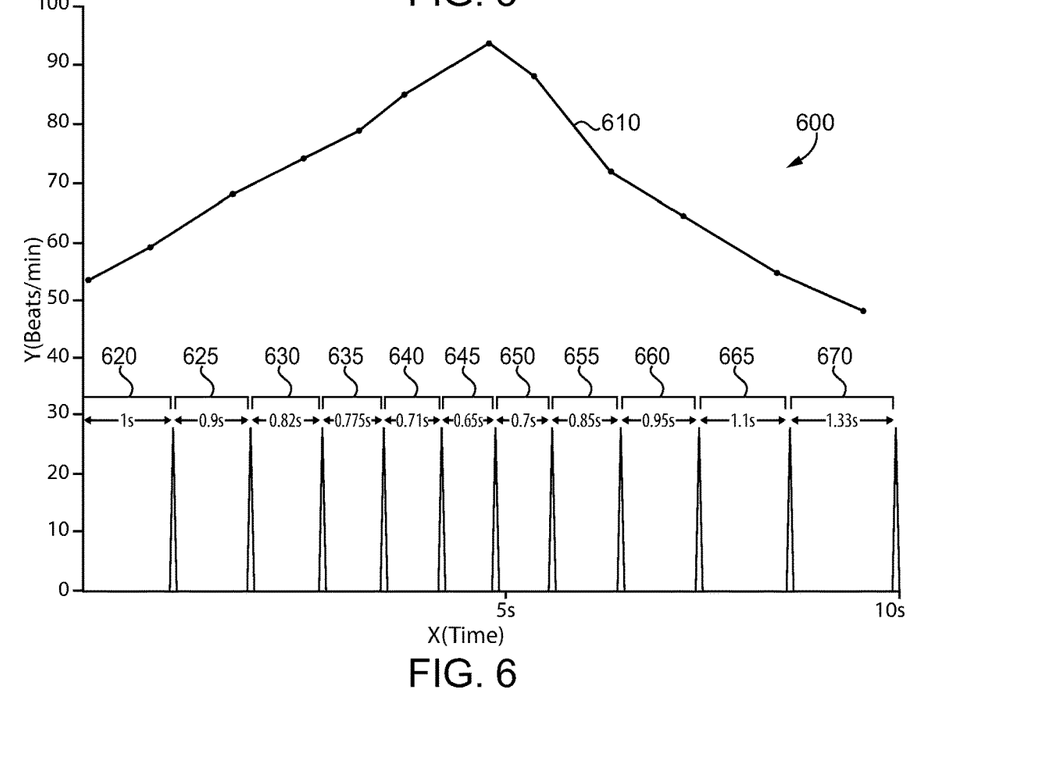
FIG. 6 is a graph of a time-varying pattern of electrical signals and heart rate variability over time where autonomic nervous system function is entrained according to yet another treatment signal.

Referring now also to FIGS. 4-6, an exemplary parasympathetic, sympathetic, and homeostatic rhythms are illustrated, respectively, wherein each of the hereinafter disclosed electrical pulses might have a stimulation frequency from about 1 Hz to about 14 Hz, although frequencies above or below this range could also be applied. Referring now to FIG. 4 in particular, there is shown heart rate in beats per minute on the Y-axis, over time (seconds) on the X-axis, with a plurality of electrical pulses separated by a time-varying duration that encodes the treatment signal. Zones A, B, C, D, E, shown with element numbers 420, 430, 440, 450, and 460, respectively, are shown between the electrical pulses, and it can be observed that the time between the pulses decreases from zone A 420 to zone C 440, then begins to increase from zone C 440 to zone E 460. The instantaneous heart rate can be seen to increase from zone A 420 to the end of zone C 440, and then decrease. This rhythmic change shown by way of a curve 410 in graph 400 occurs at the treatment signal frequency. In the context of system 10, it will be understood that control mechanism 14 is causing device 12 to deliver electrical pulses to the patient according to the time-varying pattern set forth in graph 400, at least where parasympathetic activity is targeted. Put differently, FIG. 4 shows a parasympathetic rhythm having a 4.5-second cycle (i.e., from about 0.23 to about 0.25 Hz). As can be seen, the parasympathetic rhythm may include approximately five electrical pulses during a 4.5-second cycle. At zone A 420 the pulses are separated by about 0.86 seconds, about 0.65 seconds at zone B 430, about 0.63 seconds at zone C 440, about 0.95 seconds at zone D 450, and about 1.33 seconds at zone E 460.

Referring to FIG. 5, there is shown an analogous chart or graph 500 including a curve 510, with heart rate shown on the Y-axis in comparison to time (seconds) shown on the X-axis. Curve 510 represents a sympathetic rhythm that can be used within the context of system 10 to target sympathetic activity. Individual electrical pulses are not depicted in FIG. 5, as the sympathetic rhythm of interest is a 330-second rhythm (i.e., a frequency of about 0.0033 Hz). This corresponds to about 198 pulses in 165 seconds, and thus the great number of pulses are omitted from FIG. 5 for clarity. It will nevertheless be appreciated that the pulses may start at an interval of about 1.33 seconds apart, then decrease by about 0.00344 seconds every pulse until an interval of about 0.65 seconds is reached, and then the pulse separation increased by about 0.00344 seconds every pulse to get back to an interval of about 1.33 seconds, although other variations are contemplated. Generally analogous to the changing pulse-to-pulse interval depicted in FIG. 4, the changing interval in FIG. 5 encodes a treatment signal frequency that is understood to reflect a sympathetic rhythm and entrain the SNS electrical activity toward a desired electrical activity, ultimately leading to or toward a target spectral density.

FIG. 6 depicts a graph 600 and a signal 610 where the treatment signal frequency that is encoded is reflective of a homeostatic frequency of about 0.1 Hz. Zones A, B, C, D, E, F, G, H, I, J, and K shown with element numbers 620, 625, 630, 635, 640, 645, 650, 655, 660, 665, and 670, respectively, are shown between the electrical pulses, and it can be observed that the time between the pulses decreases from zone A 620 to zone F 645, then begins to increase from zone G 650 to zone K 670. The instantaneous heart rate can be seen to increase from zone A 620 to the end of zone F 645, and then decrease. More particularly, it will be understood from FIG. 6 that starting from about a 1 second interval at zone A 620, electrical pulses can be delivered with a decreasing interval (0.9 seconds at zone B 625, 0.82 seconds at zone C 630, 0.82 seconds at zone D 635, 0.77 seconds at zone D 635, and 0.71 seconds at zone E 640) down to about 0.65 seconds at zone F 645, then increased (0.75 seconds at zone G 650, 0.85 seconds at zone H 655, 0.95 seconds at zone I 660, and 1.1 seconds at zone J 665) back up to about 1.33 seconds at zone K 670.

It should be appreciated that in addition to encoding a signal based upon the varying pulse-to-pulse interval as discussed herein, the pulse intensity can be varied. It has been observed that the amplitude of one or more of the peaks in the heart rate PQRS wave, in particular the R peak, can vary in a manner that is linked with the varying of heart rate. Leveraging this phenomenon according to the present disclosure, amplitudes of the stimulation signal could be varied in a manner that is positively correlated with an increase in pulse-to-pulse duration, for instance, or negatively correlated with an increase in pulse-to-pulse duration, potentially bringing about different or increased entrainment of ANS function and/or variability in heart rate that in turn affects ANS function.

INDUSTRIAL APPLICABILITY

Figure 7:
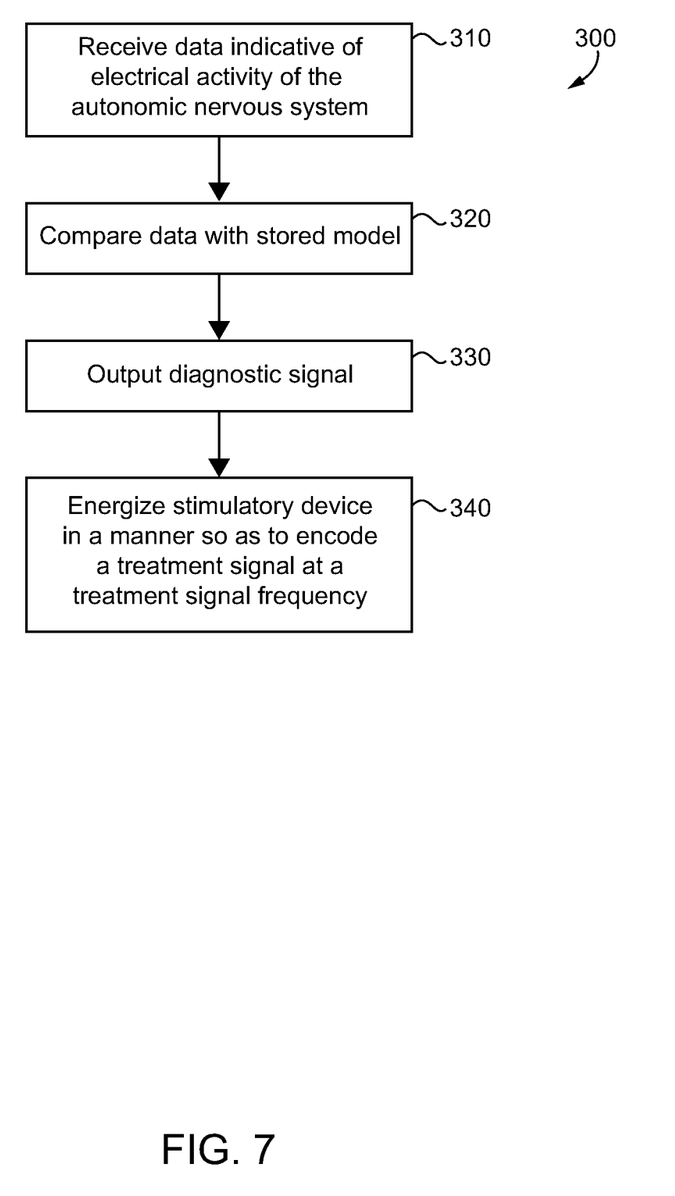
FIG. 7 is a flowchart illustrating example process and control logic flow, according to one embodiment.

Referring to the drawings generally, but in particular now to FIG. 7, there is shown example control logic and process flow in a flowchart 300. The process of flowchart 300 is shown beginning at a block 310 where data indicative of electrical activity of the ANS is received, and advances to block 320 to compare the data with a stored model. From block 320, the process advances to block 330 to output a diagnostic signal as discussed herein. From block 330, the process advances to block 340 to energize the stimulatory device in a manner so as to encode a treatment signal at a treatment signal frequency. The patient might be treated for a period of hours or even days at the desired frequency(ies). In some instances feedback and/or closed loop control with continuous or periodic gathering of data as to the spectral density produced in the ANS of the patient might be performed. It is also contemplated that frequencies might be applied to treat the patient either consecutively or concurrently.

It will be recalled that embodiments are contemplated where system 10, or analogously configured systems, are not used at all for diagnostic purposes, or are used in a manner that is different from that described in connection with the flowchart of FIG. 7. In one example, a patient can arrive for treatment at a clinician's office or treatment center and describe symptoms and/or a physical examination of the patient can be performed. The patient is then treated, based upon the expertise and knowledge of the clinician, according to one of the treatment protocols stored on computer readable memory 28.

In still other instances, control mechanism 14 could be structured so as to be configured to produce a selectable stimulatory output. Embodiments in which system 10 could be used by a patient without assistance from a medical professional or clinician (e.g., home use) are also contemplated. It is anticipated that display 34 or another user interface could include controls for selectively varying treatment signal frequencies that are provided by system 10 to device 12. It is further contemplated that a user interface could include a plurality of "knobs" such as slide controls each corresponding to frequencies in the ULF, VLF, LF, and HF bands 130, 140, 150, and 160, respectively, that can allow a user to initiate or adjust the relative intensity of electrical stimulation in and among each of the different bands. In FIG. 1 a plurality of touchscreen slide-bar controls are shown at reference numeral 36. In this manner, it will be understood that a user could set up system 10 to stimulate a patient according to a desired treatment signal frequency or frequency pattern to drive ANS activity toward a target spectral density. As also can be seen in FIG. 1, control mechanism 14, display 34, and controls 42 might reside within a common housing 44, although each may be separate in other embodiments.

The present description is for illustrative purposes only, and should not be construed to narrow the breadth of the present disclosure in any way. Thus, those skilled in the art will appreciate that various modifications might be made to the presently disclosed embodiments without departing from the full and fair scope and spirit of the present disclosure. Other aspects, features and advantages will be apparent upon an examination of the attached drawings and appended claims. As used herein, the articles "a" and "an" are intended to include one or more items, and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A system for electro-therapeutically treating a patient comprising:
    a control device having:
        a memory capable of storing a model of at least one pattern of electrical activity of a patient;
        a processor capable of receiving data indicative of electrical activity of the autonomic nervous system of a patient, comparing the received data with the stored model, generating a diagnostic signal based on the comparing of the data with the stored model, and generating a treatment signal responsive to the diagnostic signal;
        a power circuitry capable of energizing at least one stimulatory device so as to encode the treatment signal at a treatment signal frequency;
            at least one stimulatory device energized at a stimulation frequency and structured to electromagnetically couple with the nervous system of a patient and with the power circuitry of the control device;
        wherein the treatment signal frequency is less than or equal to the stimulation frequency.

2. The system of claim 1, wherein the at least one stimulatory device further includes an electrode structured for in situ electrical stimulation of a patient.

3. The system of claim 1, wherein the memory is further capable of storing a target power spectral density, and wherein the processor is further capable of receiving data indicative of power spectral density and generating a treatment signal so as to adjust the power spectral density of the autonomic system of a patient toward a target power spectral density.

4. The system of claim 3, wherein the treatment signal is in a band from about 0.003 Hz to about 0.300 Hz, from about 0.003 Hz to about 0.04 Hz, from about 0.15 Hz to about 0.4 Hz, from about 0.04 Hz to about 0.15 Hz, or about 0.0033 Hz or less.

5. The system of claim 1, wherein the processor is further capable of outputting a signal indicating which of a plurality of states of sympathetic to parasympathetic imbalance a patient falls into, as defined by a plurality of stored patterns of electrical activity in the stored model.

6. The system of claim 1, wherein the receiving of data includes receiving data produced by at least one electrical probe in contact with a patient.

7. A device for electro-therapeutic treatment of a patient, comprising:
    a memory capable of storing a target power spectral density;
    a processor capable of receiving data indicative of power spectral density, comparing the received power spectral density data with the target power spectral density, and generating a treatment signal so as to adjust the power spectral density of the autonomic system of a patient toward the target power spectral density
    a power circuit capable of energizing at least one stimulatory device so as to encode the treatment signal at a treatment signal frequency;
    wherein the treatment signal configured to shift the power spectral density of a patient among a plurality of frequency bands including an ultra-low frequency band, a very low frequency band, a low frequency band, and a high frequency band; and
    wherein the treatment signal is configured to reduce parasympathetic to sympathetic imbalance in the autonomic nervous system of a patient by way of the increasing of the power spectral density increasing the power spectral density in a first one of the plurality of frequency bands predominantly over any increase in the other ones of the plurality of frequency bands by way of entrainment of the autonomic system of a patient with the treatment signal.

8. The device of claim 7, wherein the treatment signal is configured to increase the power spectral density in the low frequency band by way of entrainment of the autonomic system of a patient, wherein the low frequency band is from about 0.04 Hz to about 0.15 Hz.

9. The device of claim 7, wherein the ultra-low frequency band is about 0.0033 Hz or less, the very-low frequency band from about 0.0033 Hz to about 0.04 Hz, the low frequency band is from about 0.04 Hz to about 0.15 Hz, and the high frequency band is from about 0.15 Hz to about 0.4 Hz.

10. A device for electro-therapeutically treating a patient, comprising:
    a control mechanism including a computer-readable memory, a computer processor, a power circuitry, and at least one stimulatory device;
    the computer-readable memory being capable of storing computer executable program instructions;
    the computer processor being capable of reading and executing the stored program instructions to generate a treatment signal and to control the power circuitry;
    the power circuitry including a power supply, the power circuitry being capable of energizing the at least one stimulatory device at a stimulation frequency that is about 1 Hz or greater and encoding the treatment signal at a treatment signal frequency that is from about 0.001 Hz to about 1 Hz; and
    the least one stimulatory device being structured to electromagnetically couple with the nervous system of the patient and to the power supply and includes at least one electrode structured for in situ electrical stimulation of the nervous system of a patient.

11. The device of claim 10 wherein the control mechanism is further structured by way of execution of the computer executable program instructions to generate the treatment signal in the form of electrical pulses produced by a stimulatory device in a time-varying pattern that defines the treatment signal frequency.

12. The device of claim 10 wherein the treatment signal frequency is in a band from about 0.003 Hz to about 0.04 Hz.

13. The device of claim 10 wherein the treatment signal frequency is in a band from about 0.15 Hz to about 0.4 Hz.

14. The device of claim 10 wherein the treatment signal frequency is in a band from about 0.04 Hz to about 0.15 Hz.

* * * * *